United States Patent [19]

Madding et al.

[11] Patent Number: 4,963,678

[45] Date of Patent: Oct. 16, 1990

[54] PROCESS FOR LARGE-SCALE PRODUCTION OF BMY 21502

[75] Inventors: Gary D. Madding; Joseph L. Minielli, both of Evansville, Ind.; Ronald J. Mattson, Meriden, Conn.

[73] Assignee: Bristol-Myers Squibb Co., New York, N.Y.

[21] Appl. No.: 427,546

[22] Filed: Oct. 27, 1989

[51] Int. Cl.$^5$ ............................................ C07D 401/14
[52] U.S. Cl. .................................................... 544/335
[58] Field of Search .......................................... 544/335

[56] References Cited

U.S. PATENT DOCUMENTS 4,826,843  5/1989  Mattson et al. ..................... 514/252

Primary Examiner—John M. Ford
Attorney, Agent, or Firm—Richard P. Ryan

[57] ABSTRACT

An improved process, suitable for adaption to large-scale manufacture for synthesis of the cerebral function enhancing agent BMY 21502.

6 Claims, No Drawings

PROCESS FOR LARGE-SCALE PRODUCTION OF BMY 21502

BACKGROUND OF THE INVENTION

This invention comprises an improved, more economical process for synthesis of BMY 21502 which is suitable for adaption to large-scale manufacture. BMY 21502 is chemically 1-[[1-[2-(trifluoromethyl)-4-pyrimidinyl]-4-piperidinyl]methyl]-2-pyrrolidinone and its synthesis and that of related compounds has been disclosed by Mattson, et al. in U.S. Pat. No. 4,826,843 issued May 2, 1989. BMY 21502 is a promising pharmaceutical agent which enhances cerebral functioning, improves memory and learning, and reverses amnesias. Currently BMY 21502 is undergoing clinical trials designed to confirm its safety and efficacy as an ethical pharmaceutical.

The demand for drug substance has increased substantially with the advent of clinical testing and future need for much larger amounts is projected due to the intended commercialization of BMY 21502. The prior art process for preparation of BMY 21052 (Scheme A) proved to be unsatisfactory for adaptation to the larger scale processing required to meet these demands for large quantities of the drug.

cal intermediates generally require synthesis of these intermediates for larger scale processes.

It is further appreciated by those skilled in process development that many processes, procedures, and/or reactions are not amenable to being carried out on a large scale as is done in a pilot plant or a manufacturing facility. Some examples of situations where scale-up can be problematic may involve the use of hazardous or toxic reagents and/or solvents; highly exothermic reactions; high pressure or high vacuum processes, such as those required for certain high pressure reactions or high vacuum distillations; chromatographic separation and/or purification; reduced yield on scale-up and the like. A more recent consideration for large scale operations is the limitations which have been set on certain emissions as well as the disposal of waste products from chemical processing. Processes involving these elements incur higher levels of cost in production.

The prior art process for preparation of BMY 21502 is not amenable to scale-up for many of the reasons listed above as well as other process problems unique to the actual reactions employed.

Preparation of the 2-pyrrolidinone anion (in Step 1) is accompanied by evolution of hydrogen gas. In this particular instance a large formation of a stable foam also occurs and its presence causes the stoppage of

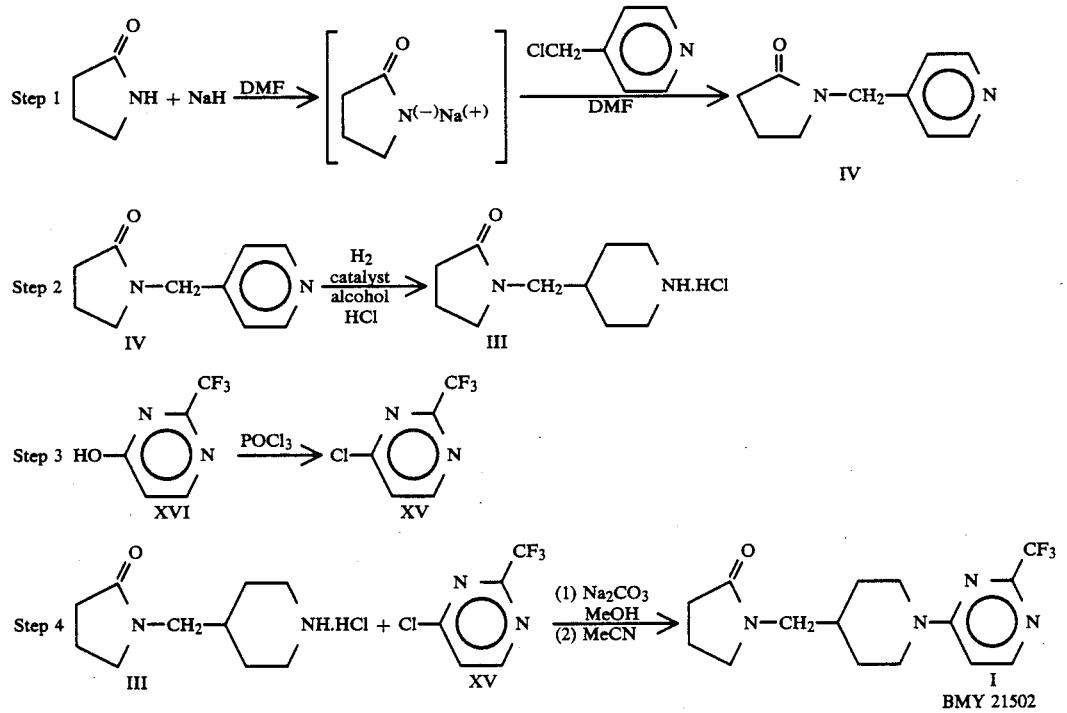

SCHEME A
PRIOR ART PROCESS

The laboratory scale process disclosed in U.S. Pat. No. 4,826,843 did not include step 3 of Scheme A because commercially available 4-chloro-2-trifluoromethylpyrimidine was employed. This intermediate can also be synthesized by readily available literature methods, e.g., *J. Org. Chem.* 26/4504 (1961). Various halopyrimidines can be obtained commercially in laboratory quantities. It is appreciated by those familiar with chemical process scale-up that price considerations and lack of availability of bulk quantities of required chemi- further addition of 2-pyrrolidinone in order to prevent spillover of the reactants.

Reduction of the pyridine intermediate IV in Step 2 does not proceed very well on a larger scale if IV is not purified by vacuum distillation prior to its reduction.

In Step 3 the major problem concerns bulk preparation of the starting 4-hydroxy-2-trifluoromethylpyrimidine, XVI. Prior synthesis of this chemical intermediate is necessary to provide the quantities required for large-scale production. The available synthetic routes to XVI all employ either trifluoroacetonitrile ($CF_3CN$; an expensive noxious gas) or its derivative, trifluoroacetamidine ($CF_3C(NH)NH_2$; also expensive, noxious, and with limited stability) as the synthetic source for the trifluoromethyl moiety in XVI.

Finally in Step 4, purification of the target product, BMY 21502, requires chromatographic purification, an important limiting factor for scale-up.

An objective then of the present invention is to provide a chemical process which can be operated on a large scale. A second objective is to provide a chemical process whose cost considerations allow its utilization on a large scale to be economical.

SUMMARY AND DETAILED DESCRIPTION OF THE INVENTION

This invention relates to an improved synthetic process which can be adapted for large-scale preparation of 1-[[1-[2-(trifluoromethyl)-4-pyrimidinyl]methyl]-2-pyrrolidinone (BMY 21502), a compound possessing useful psychocognitive properties. This improved process offers advantages in economies of reagents, time and labor costs as well as increased suitability for use with standard larger-scale chemical process equipment.

The improved process also comprises incorporation of several novel processing modifications in certain of the reaction sequences previously disclosed and it is these modifications which in part allow the subject process to be adapted to the large scale required for commercialization. It should be appreciated that cost of goods is a major consideration in commercialization of a product and modifications which improve cost efficiency in production become extremely important.

The improved process of this invention allowing efficient scale-up is outlined in Scheme B.

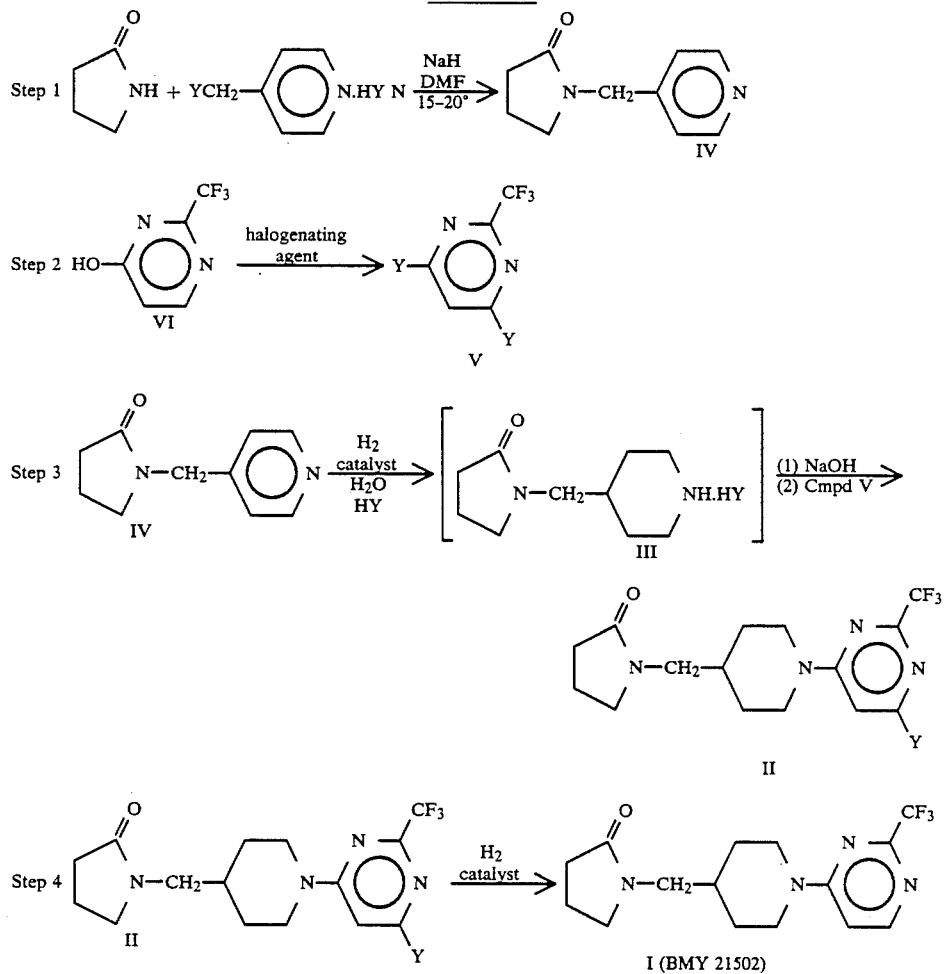

SCHEME B

In Scheme B, Y is halo (chloro, bromo or iodo) with chloro preferred. It would be expected that other suitable organic synthetic leaving groups would also function similarly in place of Y, the displaceable halo group.

The initial step of the original process involved formation of the anion of 2-pyrrolidinone by reaction in DMF with NaH. The chloromethylpyridine acid addition salt (HCl preferred) starting material was then introduced for reaction with the anion to produce intermediate compound IV. Formation of the anion with the concomitant evolution of hydrogen is accompanied by considerable foam formation and the stability of this foam and its accumulation halts the addition of 2-pyrrolidinone. The stable foam acts to preclude completion of the reaction in a reasonable time when carried out on a large scale.

Various modifications were attempted in the search for overcoming the foaming problem. These attempted modifications either failed to minimize foaming or caused additional problems for a scaled-up process. Initial modification attempts dealt with the nature of the reaction liquid medium. Substitution of other organic liquids for DMF resulted in a reduction of the solvent efficiency possessed by DMF and this led to solidification of the reaction mixture as part of a strongly exothermic process. Elimination of the mineral oil from the sodium hydride reagent had little effect on foaming on a large scale. Similarly, substitution of other strong bases such as sodium isopropoxide, KH and $LiNH_2$ resulted in no intermediate compound IV being isolable. Experimentation indicated that the stable foam formation might be attributable to the surfactant properties of the pyrrolidinone anion in DMF. However, reverse addition (chloromethylpyridine hydrochloride added first to the sodium hydride-DMF slurry followed by the 2-pyrrolidinone starting material) resulted in reduced product formation and apparent polymerization of the chloromethylpyridine reagent when the reaction was carried out on a larger scale. The foam problem, which prevented scale-up, was finally eliminated by the unobvious modification in which a mixture of approximately equal parts of 2-pyrrolidinone and chloromethylpyridine hydrochloride were added to a DMF suspension of sodium hydride at a temperature of about 0°–20°. Product yield is reduced at temperatures exceeding 20° while at temperatures below about 0° the reaction rate is slowed sufficiently to allow accumulation of the starting materials thereby creating potential for uncontrolled, runaway reaction when carried out on a large scale.

Another problem in preparation and subsequent use of intermediate IV in a large scale process is that intermediate IV was originally purified by a vacuum distillation and without this purification step the subsequent process for reduction of compound IV does not work very well. It was discovered that by extracting the reaction residue of Step 1 of the improved process with hot isopropyl ether, suitably purified compound IV could be obtained without the required vacuum distillation.

Another inherent problem of the prior art process concerned the availability of hydroxypyrimidine intermediate XVI, which was used in Step 3 to prepare the coupling component compound XV. The process previously employed for its production is shown below in Scheme C.

Scheme C
Synthesis of Intermediate XVI

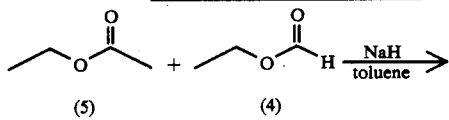

(5)   (4)

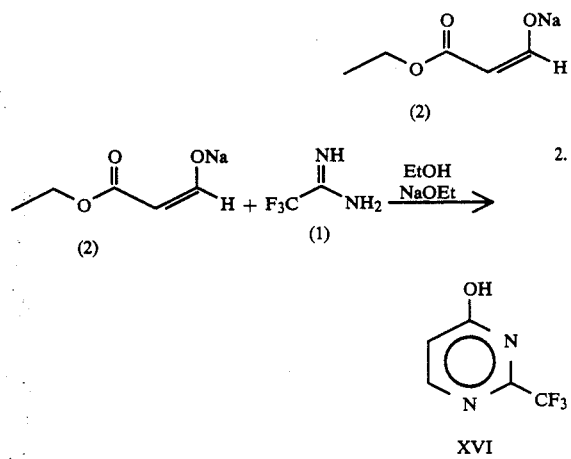

The synthesis set forth in Scheme C is known in the art: ethyl acetate and ethyl formate are condensed to form formylethyl acetate in the form of its sodium salt which is then cyclized with trifluoroacetamidine to give the desired hydroxypyrimidine intermediate (XVI). One of the problems with this pathway is that sodium formylethyl acetate is unstable and decomposes when isolated thereby making it a low yield intermediate for subsequent reaction. On a larger scale, this results in significant production and handling problems. Another problem in using this pathway concerns the reagent trifluoroacetamidine (1). When purchased, (1) is very expensive and when prepared prior to use (Reilly and Brown, *J. Am. Chem. Soc.*, 78, 6032 (1956)) its synthesis requires another expensive starting material, trifluoroacetonitrile, which is a low-boiling (−64°), toxic gas. Not only does the preparation of (1) require low temperatures which are unobtainable in most plant equipment (−70°) but the handling of the trifluoroacetonitrile on a large scale poses a safety problem. As a final consideration, the acetamidine intermediate (1) also lacks stability thereby limiting shipment and storage. In light of these problems, utilization of the hydroxy-pyrimidine intermediate XVI poses a major problem for development of a large scale process for production of BMY 21502.

These problems have been overcome in developing the improved process. It utilizes a dihydroxypyrimidine intermediate, VI, as a starting material. The preparation of VI has been reported in the literature: Path a. Scheme D (S. Inoue, A. Saggiomo and E. Nodiff, *J. Org. Chem.*, 1961, 26, 4504) and Path b. Scheme D (G. Kheifets, Zh. Org. Khim. (Eng. trans.), 1975, 15(8), 1564–71).

Scheme D
Synthesis of Intermediate VI

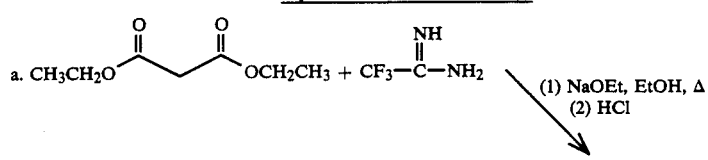

Scheme D
Synthesis of Intermediate VI

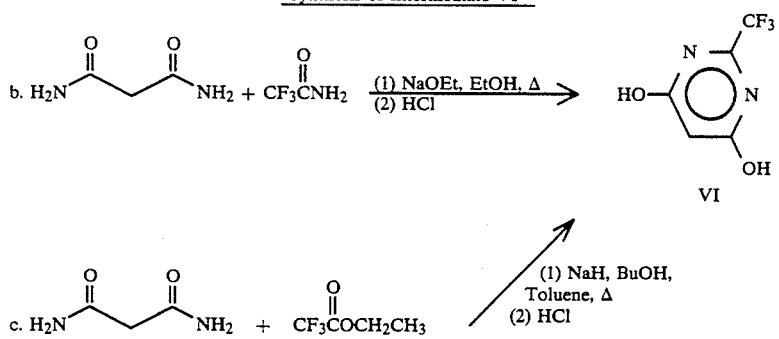

Path a. still uses the expensive trifluoroacetamidine, and Path b. presents processing difficulties. Therefore, Path c. was developed, in which ethyl trifluoroacetate was substituted for trifluoroacetamide. The reaction parameters were also modified. Compound VI is then available in 44% yield from inexpensive, readily available and relatively non-toxic starting materials.

Halogenation of VI with an appropriate halogenating reagent, as would be known to one skilled in organic synthesis, (cf. Inoue, et al.) smoothly yields the dihalo intermediate V in Step 2 of the improved process. In practice, $POCl_3$ is preferred as a halogenating agent to provide V wherein Y is chloro.

Steps 2 and 4 of the prior art process (Scheme A) are combined and carried out in water as step 3 of the instant improved process (Scheme B). This combination step conveniently produces the halogenated precursor II of BMY 21502 by straightforward low pressure hydrogenation of IV, removal of catalyst and addition of a small amount of acetonitrile and intermediate VI to the basified aqueous solution of III. The intermediate product II precipitates after formation and is isolated by simple filtration. Improved process Step 3 results in a considerable saving of labor, reagents and process time. The added acetonitrile, in an amount of about 10% of solvent volume, seems to enhance the coupling process and thereby enhances product yield.

The hydrogenation catalyst of Step 3 may be selected from among the group of standard hydrogenation catalysts, generally containing platinum or palladium. Preferred catalysts are platinum IV oxide and platinum on carbon.

Carrying out the reduction in water, which is much cheaper, non-flammable and easily disposable; followed by direct coupling in the water solution is a major improvement in the new process. In contrast the old process involved reduction in alcohol; isolation of intermediate product; coupling in a heterogenous reaction mixture (solid sodium carbonate and DMF); filtration; in vacuo removal of DMF; and, as a minimum, recrystallization of product from an organic solvent. In the previously disclosed process, most of the diazine products prepared in this manner required chromatography for separation/purification. As mentioned earlier, chromatographic processes are best avoided on larger scale preparations. In Step 3 of the improved process the overall yield and purity (without chromatography) of the product are both increased as are efficiencies in labor, materials and process time mentioned above. As a result processing through-put is increased.

The final step of the improved process (Step 4) involves catalytic hydrogenolysis of the pyrimidine ring halogen atom to provide the target BMY 21502. While hydrogenolysis can be effected using the standard catalysts for this process such as Raney nickel or palladium catalysts, a preferred catalyst is palladium on carbon. Other chemical reagents can effect the same conversion such as, e.g. zinc and acid, but catalytic hydrogenolysis is preferred.

To summarize the foregoing, there is described an improved process for large-scale production of BMY 21502 comprising 4 steps:

(1) Adding an equimolar mixture of 2-pyrrolidinone and 4-halomethylpyrimidine hydrohalide to a suspension of NaH in DMF at 0°–20° to form 1-(4-pyridinyl-methyl)-2-pyrrolidinone (IV).

The intermediate product IV is obtained in form suitable for use in Step 3 by filtering the Step 1 reaction mixture and concentrating the filtrate in vacuo to a residue. Extraction of the residue with hot isopropyl ether provides IV by filtration of the chilled isopropyl ether extracts.

(2) halogenating 4,6-dihydroxy-2-trifluoropyrimidine (VI), prepared from malonamide and ethyl trifluoroacetate; with a suitable halogenating agent to give 4,6-dihalo-2-trifluoropyrimidine (V). Typical halogenating agents would be, for example, phosphorus oxychloride or oxybromide, phosphorous pentachloride, diphenyl phosphonochloride and the like. The preferred intermediate compound V is the dichloro derivative which is preferably synthesized with $POCl_3$.

(3) catalytically hydrogenating an aqueous solution of IV under low pressure to give III which is basified and treated with the dihalopyrimidine intermediate V to provide the penultimate compound II.

(4) converting II by catalytic hydrogenolysis to the ultimate product, BMY 21502.

This improved process meets the stated objectives of providing a practical synthetic process which can be utilized economically on the large scale required for production of BMY 21502. This process is essentially a four step process compatible with large scale chemical processing equipment. Process modifications have been discovered and incorporated which:

control the formation of reaction limiting foam in Step 1.
eliminate vacuum distillation and chromatographic purification requirements without a decrease in yield.
replace organic solvents with water.
minimize isolation and purification of reaction intermediates.

provide the final product in improved yield and purity and at lower cost.

DESCRIPTION OF SPECIFIC EMBODIMENTS

The process of this invention is illustrated in greater detail by the following examples directed to preferred embodiments of the hereinabove described process steps. These examples, however, should not be construed as limiting the scope of the present invention in any way.

EXAMPLE 1

1-(4-Pyridinylmethyl)-2-pyrrolidinone, Compound IV, Step 1

To a stirred suspension of sodium hydride (60% dispersion in mineral oil, 9.4 kg, 235 moles) in N,N-dimethylformamide (119 kg, 125 L) was added, in 8 mole portions, a mixture of 2-pyrrolidinone (10 kg, 117.5 moles) and 4-chloromethylpyridine hydrochloride (19.3 kg, 117.5 moles) while starting with reaction temperature at 0° and letting the temperature rise to 15° and then maintaining it at 15°. The addition took 3 hrs., adding as rapidly as temperature and foaming control would permit. The reaction mixture was stirred at approximately 25° for 16 hrs. Next, the mixture was clarified by filtration through diatomaceous earth. The solids were discarded. The filtrate was concentrated in vacuo and the residue was extracted with boiling isopropyl ether (2×167 L). The combined extracts were heated to boiling and the solution was cooled slowly to 30°. The product precipitated. The mixture was stirred for 16 hrs. and then cooled to 5° for 3 hrs. The compound III was isolated by filtration and dried in vacuo at 30° to give 16 kg product, 77.7% yield.

Anal. Calcd. for $C_{10}H_{12}N_2O$: C, 68.16; H, 6.87; N, 15.90.

Found: C, 67.93; H, 6.78; N, 15.78.

EXAMPLE 2

4,6-Dichloro-2-trifluoromethylpyrimidine, Compound V, Step 2

4,6-Dihydroxy-2-trifluoromethylpyrimidine (VI; 540 g; 3.0 M) was stirred with phosphorous oxychloride (1300 mL; 2147 g; 14.0 M) in a 5 L round-bottom flask with mechanical stirrer and triethylamine (607 g; 6.0 M) was added over 1 hr. After the exotherm, the reaction was heated on a stem-bath for 3 hr. The reaction mixture was cooled to 40°, and then it was poured with stirring into a mixture of 10 kg ice and 2 kg water. The mixture was extracted with 4×0.5 L methylene chloride. The combined extracts were dried (MgSO4) and filtered. The filtrate was concentrated in vacuo to give the crude compound V. When further purification was desired, the crude V was distilled at 48°-50°/2 mm using a steam-bath (Lit. b.p. 38°/1 mm) to give a colorless liquid. The purified yield was 78.8%.

Anal. Calcd. for $C_5HCl_2F_3N_2$: C, 27.68; H, 0.47; N, 12.91.

Found: C, 27.45; H, 0.39; N, 12.86.

IR and NMR are consistent.

EXAMPLE 3

4,6-Dihydroxy-2-trifluoromethylpyrimidine, Compound VI, starting material for Step 2

Sodium hydride (900 g, 57.5% dispersion in mineral oil; 518 g active NaH; 22.5M) was stirred with 7.5 L toluene in a 22 L round-bottomed flask. Butanol was added over 5 hr. so that the pot temperature was maintained at 40°. The mixture was stirred an additional 16 hr. Malonamide (765 g; 7.5 M) was added, followed by ethyl trifluoroacetate (1065 g; 7.5 M). The ensuing reaction was exothermic; the mixture was then heated on a steam-bath for 3.5 hrs. It was then stirred at 23°-25° for an additional 16 hrs. The mixture was extracted with water (1×4 L and 1×2 L). The combined aqueous extracts were treated with activated charcoal and filtered. The filtrate was maintained at 10°-15° as it was acidified to pH 1-2 with 37% hydrochloric acid. The mixture was chilled to 5°. The solid was isolated by filtration and dried at 50° in vacuo to give 600 g (44.4% yield) VI m.p. 255°-256° (Lit. 265°).

EXAMPLE 4

1-[[1-[6-Chloro-2-(trifluoromethyl)-4-piperidinylmethyl]-2-pyrrolidinone, Compound II, Step 3

To a solution of 1-(4-pyridinylmethyl)-2-pyrrolidinone (Intermediate compound IV, 905 g, 5.14 moles) in potable water (11 L) was added reagent grade hydrochloric acid (470 mL, about 5.65 moles) and platinum IV oxide (25 g). The stirred mixture was treated with hydrogen at low pressure (5 inches of water pressure) and after hydrogen uptake was complete (about 3 days) the catalyst was removed by filtration and sodium hydroxide (50% solution, 130 g, 14.1 moles) was added. Next acetonitrile (1.68 L) was added and the solution was cooled to 25° while rapidly stirring and 5.14 moles of 4,6-dichloro-2-trifluoromethylpyrimidine, V, was added dropwise over a period of about 2 hours. The temperature is generally held at or below 25° during this addition. The product separates during this addition or on continued stirring overnight and can be removed by filtration.

The solid was rinsed well with water on the filter and then dried in air overnight to provide an 85% yield of the penultimate compound, II. A sample was dried in a 50° vacuum oven for 4 hrs., with no weight loss observed, and then submitted for analysis.

Anal. Calcd. for $C_{15}H_{18}ClF_3N_4O$: C, 49.66; H, 5.00; N, 15.04.

Found: C, 49.32; H, 4 94; N, 15.65.

The IR and NMR were consistent.

EXAMPLE 5

1-[[1-[2-(Trifluoromethyl)-4-pyrimidinyl]-4-piperidinyl]-methyl]-2-pyrrolidinone BMY 21502 Compound I Step 4

The penultimate intermediate chloro compound (Compound II, 43.6 g, 0.12 M) was stirred in 500 mL absolute ethanol, 21.8 g sodium carbonate, and 3 g 10% Palladium on carbon. The flask was charged with excess hydrogen capacity and stirred overnight.

A teaspoon of Celite was added to the flask and the catalyst filtered through a Celite pad using fiber-glass paper. The colorless ethanol solution was concentrated to 40.5 g off-white solid. This was dissolved in 300 mL water and acidified with 6N hydrochloric acid to pH 1. The mixture was filtered, chilled (ice bath), and neutralized with 4N NaOH solution while stirring. At near neutral, a small amount of sodium bicarbonate solution was added and the resulting mixture was kept at 5° for 16 hrs. The white solid was collected by filtration and rinsed two times with 50 mL water and air dried to 39 g. Further drying in a 50° vacuum oven for 16 hrs gave 37.2 g (94% yield) of the target product, BMY 21502.

Anal. Calcd. for $C_{15}H_{19}F_3N_4O$: C, 54.87; H, 5.83; N, 17.06.

Found: C, 54.83; H, 5.70; N, 16.73.

The IR and NMR was consistent.

What is claimed is

1. An improved process suitable for large-scale production of BMY 21502.

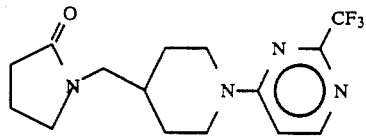

BMY 21502 comprising the steps of (a) adding a mixture of 2-pyrrolidinone and 4-halomethylpyridine to a suspension of sodium hydride in N,N-dimethylformamide at about 15° to 20° to form 1-(4-pyridinylmethyl)-2-pyrrolidinone (IV)

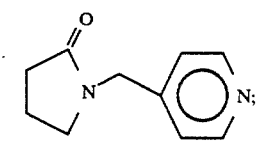                                     IV (b) catalytically hydrogenating an acidified aqueous solution of IV giving III

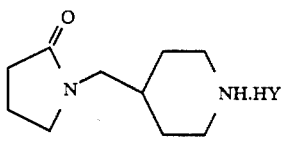                                     III wherein Y is chloride, bromide or iodide, and basifying the aqueous solution and adding V

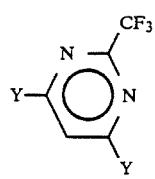                                     V to produce intermediate II

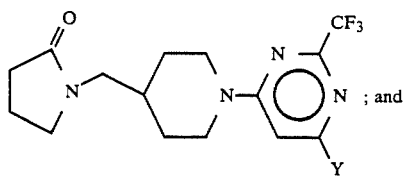                                     II ; and (c) converting II by catalytic hydrogenolysis to the product BMY 21502.

2. An improved process suitable for large-scale production of BMY 21502.

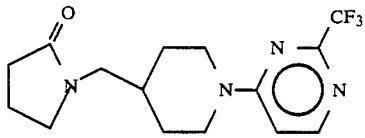

BMY 21502 comprising the steps of (a) adding a mixture of 2-pyrrolidinone and 4-halomethylpyridine to a suspension of sodium hydride in N,N-dimethylformamide at about 15° to 20° to form 1-(4-pyridinylmethyl)-2-pyrrolidinone (IV)

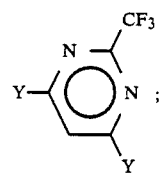                                     IV (b) halogenating 4,6-dihydroxy-2-trifluoropyrimidine with a halogenating agent to give 4,6-dihalo-2-trifluoropyrimidine V.

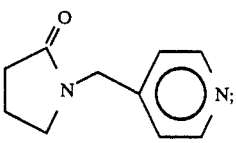                                     V (c) catalytically hydrogenating an acidified aqueous solution of IV giving III,

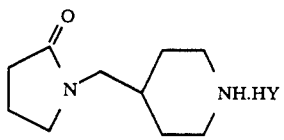                                     III wherein Y is chloride, bromide or iodide, and basifying the aqueous solution and adding V to produce intermediate II

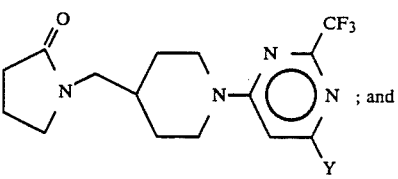                                     II (d) converting II by catalytic hydrogenolysis to the product BMY 21502.

3. The process of claim 2 wherein Y is chloride.

4. The process of claim 2 wherein the halogenating agent in step (b) is phosphorus oxychloride.

5. The process of claim 2 wherein that hydrogenation catalyst in step (c) is platinum IV oxide.

6. The process of claim 2 herein 10% palladium on carbon catalyst is used in the catalytic hydrogenolysis of step (d).

* * * * *